US00PP15688P3

(12) United States Plant Patent
Stemkens

(10) Patent No.: US PP15,688 P3
(45) Date of Patent: Mar. 22, 2005

(54) *VERBENA* PLANT NAMED 'DARLENA'

(50) Latin Name: *Verbena×hybrida*
Varietal Denomination: Darlena

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 45 days.

(21) Appl. No.: 10/342,814

(22) Filed: Jan. 15, 2003

(65) Prior Publication Data

US 2004/0139521 P1 Jul. 15, 2004

(51) Int. Cl.[7] ..... A01H 5/00

(52) U.S. Cl. ..... Plt./308

(58) Field of Search ..... Plt./308

(56) References Cited

PUBLICATIONS

GTITM UPOVROM Citation for 'Darlena' as per NL PBR ZHD0087; Dec. 28,2000.*

* cited by examiner

*Primary Examiner*—Kent Bell
*Assistant Examiner*—Louanne Krawczewicz Myers
(74) *Attorney, Agent, or Firm*—Edouard G. Lebel

(57) ABSTRACT

A new and distinct variety of *Verbena* plant particularly distinguished by its neonrose flowers, early flowering, and a spreading habit that is first semi-erect and later spreading.

1 Drawing Sheet

Botanical classification: *Verbena×hybrida.*
Varietal denomination: 'Darlena'.

BACKGROUND OF THE NEW PLANT

The present invention comprises a new distinct cultivar of *Verbena,* botanically known as *Verbena×hybrida.*

The new cultivar is propagated from cuttings resulting from the cross of 'W720' and 'T593'. 'W720' is a rose flowering *Verbena* having a spreading habit. 'W720' is not commercially available and is not known by any synonyms. 'T593' is a scarlet flowering *Verbena* having a semi-erect habit. 'T593' is not commercially available and is not known by any synonyms. Neither 'W720' nor 'T593' has been patented.

As a result of this cross the present cultivar was created in 1999 in Enkhuizen, Netherlands and has been repeatedly asexually reproduced by cuttings in Enkhuizen, Netherlands and Sarrians, France over a three-year period. It has been found to retain its distinctive characteristics through successive propagations, and this novelty appears to be firmly fixed.

'Darlena' is closely related to the patented variety Florena (U.S. Plant Pat. No. 11,095), from which it differs in vigor, flower color and length of spikes.

This new *Verbena* plant is an annual in most climatical zones in the U.S., only in zones 9 and 10 it is a perennial plant.

DESCRIPTION OF THE DRAWING

This new *Verbena* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Verbena.* The data which defines these characteristics were collected from asexual reproductions carried out in Enkhuizen, Netherlands. The plant history was taken on 14 weeks old plants, blossomed under natural light in a greenhouse and grown in a 10.5 cm container.

Color readings were taken in the greenhouse under ambient light. Color references are primarily to The R.H.S. Colour Chart of The Royal Horticultural Society of London.

Differences between the new cultivar 'Darlena,' its parents and a similar cultivar

| | 'Darlena' | 'W720' | 'T593' | 'Temari coral rose' |
|---|---|---|---|---|
| Flower color | Neon rose | Rose | Scarlet | Coral rose |
| Earliness | Early | Very early | Late | Late |
| Seed set | No | No | Much | Abundant |
| Leaf incision | Double incised | Double incised | No incisions | No incisions |

The commercial name of the most resembling variety is 'Temari coral rose.' The variety name of this patented variety is 'Sunmariripi' and its U.S. Plant Pat. No. is 11,037.

The Plant

Classification:

*Botanical.*—*Verbena×hybrida.*

Parentage:

*Female parent.*—A seedling named 'W720' is one of our seedlings from our W-generation of plants bred in 1994.

*Pollen parent.*—A seedling named 'T593' is one of our seedlings from our T-generation of plants bred in 1991.

Growth habit: Semi-correct, later spreading.

Plant height: 16–24 cm.
Speading area of plant: 35–65 cm.
Growth rate: Hanging and vigorous.
Strength: Resistant to hot and cold weather.
Branching character: Freely branching and lateral branching at every node.
Blooming period: From April until November.

The Stem

Diameter: 2–2.5 mm.
Length: 10–15 cm.
Shape: Tetragonal.
Color of the stem: 141C.
Anthocyanin pigmentation: Present, color 180D.
Length of internode: 25–40 mm, depending on the light where the plant is propagated.
Pubescence: Pubescence is present.
Length lateral branches: 15–25 cm.

The Foliage

Phyllotaxis: Opposite.
Shape of blade: Broadly ovate.
Texture:
*Upper side.*—Smooth.
*Lower side.*—Smooth.
Venation: Pinnate.
Leaf margin: Laciniate.
Leaf base: Hastate.
Leaf apex: Apiculate.
Length: 16–28 mm.
Width: 14–24 mm.
Depth of incision: 8–12 mm.
Color:
*Upper side.*—141C.
*Lower side.*—138B.
Pubescence: Some pubescence is present.
Length of leaf stem: 8–15 mm.
Petiole surface structure: Slightly pubescent.
Petiole diameter: 2–4 mm.
Petiole coloration: 141C.

The Bud

Peduncle length: 30–40 mm, depending on season.
Peduncle diameter: 2–3 mm.
Peduncle color: 137C.
Size of the bud:
*Length.*—8–12 mm.
*Diameter.*—2 mm.
Shape: Elongated and ovate.
Color: 137D.
Sepals:
*Color* (*upper side*).—138B.
*Color* (*lower side*).—138C.
*Form.*—Upright.
*Number.*—5, fused.
*Length.*—6–7 mm.
*Width.*—2 mm.
*Shape.*—Elongated.
*Apex.*—Emarginate.
*Base.*—Fused.
*Margin.*—Entire.

The Flower

Facing direction: Upward.
Outward curvature of petal: Slightly curved.
Flower diameter: 14–20 mm.
Flower height: 14–18 mm.
Flower tube length: 13–17 mm.
Flower throat diameter: 2 mm.
Borne: In a cluster.
Form: Salverform; sessile on terminal spikes.
Petal color:
*Upper side.*—67A, a bit more blue.
*Lower side.*—67C.
Eye: A very small (1 mm) greenish Eye (155B) is present. Typically three out of the five petals exhibit this greenish coloration on the upper side of them.
Overlapping of the petals: Separate.
Number of petals: Gamopetalous, five lobed.
Shape of the petals: Each petal is heart shaped at the apex and grown together at the base.
Petal apex: Emarginate.
Petal base: Fused.
Petal margin: Entire.
Petal surface texture: Smooth.
Size of the petal:
*Length.*—5–7 mm.
*Width.*—6–8 mm.
Inflorescence:
*Length.*—35–45 mm.
*Diameter.*—30–40 mm.
Calyx length: 8–10 mm.
Calyx diameter: 2–3 mm.
Anthocyanin pigmentation of calyx limb: Absent.
Color of the calyx: 138C (outside surface).
No. of flowers per inflorescence: 25–35.
Fragrance: No fragrance.
Bloom time of one inflorescence: New florets continue to open over a period of 14 days.
Lastingness of one flower: 2–4 days.

The Reproductive Organs

Androecium:
*Stamen quantity.*—Four.
*Anther shape.*—Ovoid.
*Anther length.*—1 mm.
*Anther color.*—144C.
*Amount of pollen.*—No pollen.
Gynoecium:
*Pistil quantity.*—1.
*Stigma shape.*—Bi-lobed.
*Pistil length.*—1.8–2.2 mm.
*Stigma color.*—144C.
*Style length.*—1.6 cm.
*Style color.*—144D.
*Ovary color.*—144C.

The Seed

Seedset: No seedset has been observed.

The Roots

Type of roots: Fibrous. Roots starts to grown on every part of the stem That contacts the soil, so not only at the nodes.
Physiological and ecological characteristics: Good tolerance to heat and cold. Strong resistance to pests and diseases, particularly powdery mildew.

What is claimed is:

1. A new and distinct cultivar of *Verbena* plant named 'Darlena', substantially as illustrated and described herein.

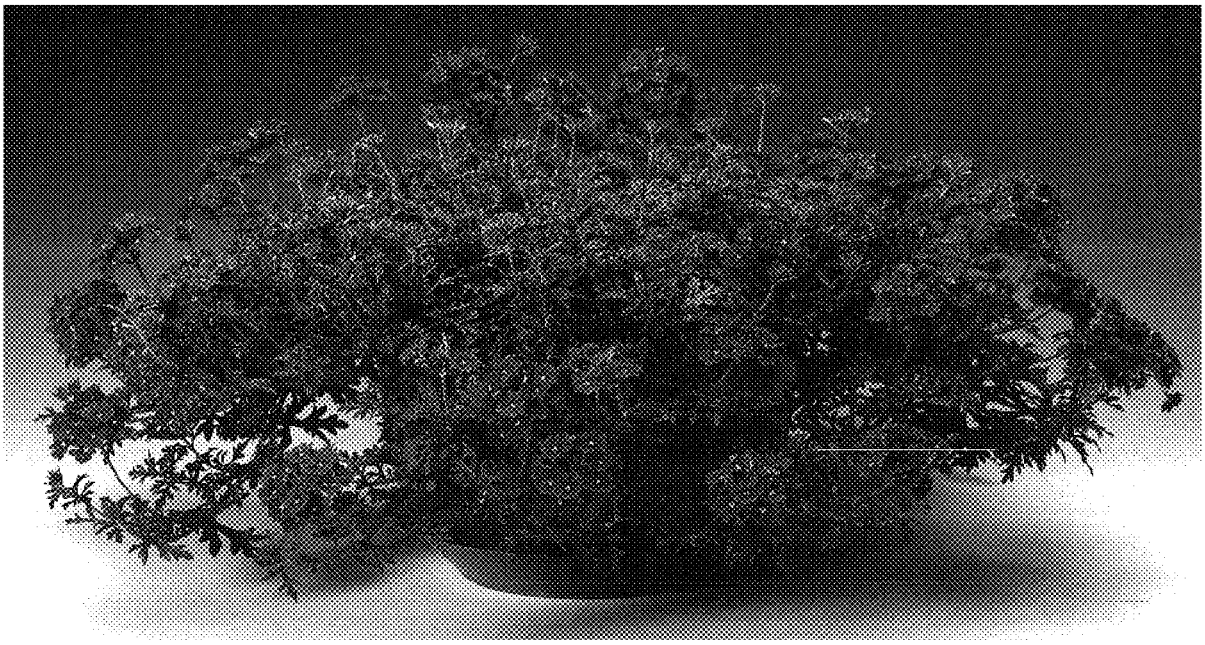

* * * * *